United States Patent [19]

Meyer et al.

[11] 4,218,197
[45] Aug. 19, 1980

[54] COMBINED PERISTALTIC PUMP AND VALVE FLOW CONTROLLER

[75] Inventors: Richard C. Meyer; Edmund E. Buzza, both of La Habra, Calif.

[73] Assignee: Beckman Instruments, Inc., Fullerton, Calif.

[21] Appl. No.: 922,457

[22] Filed: Jul. 6, 1978

[51] Int. Cl.² ............... F04B 43/12; F04B 45/08; G01N 27/26
[52] U.S. Cl. ................... 417/442; 417/477; 204/195 G
[58] Field of Search ............ 417/474, 475, 476, 477, 417/236, 442; 204/195 P, 195 S, 195 M, 195 R; 422/103, 100, 82; 137/147–150

[56] References Cited

U.S. PATENT DOCUMENTS

| | | | |
|---|---|---|---|
| 1,703,361 | 2/1929 | Pohl | 417/477 X |
| 3,431,864 | 3/1969 | Jones | 417/477 |
| 3,542,491 | 11/1970 | Newman | 417/477 X |
| 3,628,891 | 12/1971 | Isreeli et al. | 417/476 X |
| 3,723,030 | 3/1973 | Gelfand | 417/475 |
| 3,730,650 | 5/1973 | Kling | 417/475 |
| 3,768,934 | 10/1973 | Magerle | 417/471 |
| 3,787,148 | 1/1974 | Kopf | 417/477 |
| 3,829,251 | 8/1974 | Schwing | 417/477 |
| 3,832,096 | 8/1974 | Gelfand | 417/477 X |
| 3,869,354 | 3/1975 | Montalvo | 204/195 P X |
| 3,997,420 | 12/1976 | Buzza | 324/30 R X |
| 4,070,725 | 1/1978 | Austin et al. | 417/477 X |

FOREIGN PATENT DOCUMENTS 2553880  6/1977  Fed. Rep. of Germany ......... 417/442

*Primary Examiner*—Richard E. Gluck
*Attorney, Agent, or Firm*—Robert J. Steinmeyer; Robert R. Meads; John R. Shewmaker

[57] ABSTRACT

Apparatus for conveying a blood sample through a flow cell which measures characteristics such as pH, $PCO_2$, and $PO_2$ of the sample and for pumping a wash solution through the cell between samples. The flow cell inlet is selectively connected (1) to a sample-filled syringe for driving sample through the flow cell or (2) to a reservoir of the wash solution. The flow cell outlet is connected by a conduit to a waste receptacle. A rotor of a combined peristaltic pump and valve coacts with an elastomeric tubular section of the conduit. The rotor and the elastomeric section are movable in a transverse direction relative to each other between (1) a first or pumping position wherein the rotor compressively engages the section for pumping fluid wash solution through the cell and the conduit and (2) a second or relaxed position wherein the rotor is released from the section to provide an open unrestricted channel for the flow of sample driven by the syringe through the cell.

8 Claims, 4 Drawing Figures

COMBINED PERISTALTIC PUMP AND VALVE FLOW CONTROLLER

BACKGROUND OF THE INVENTION

1. Field of the Invention

The present invention relates generally to fluid flow control systems and, more particularly, to flow controllers employing peristaltic pumps. The invention is particularly advantageous for use in conveying biological or biochemical fluids such as blood or other fluids known to clog or corrode elements of prior flow controllers.

2. Description of the Prior Art

U.S. Pat. No. 3,997,420, assigned to the assignee of the present invention, describes a flow cell for use in blood chemistry analyses and in particular for determining the pH, $PCO_2$ and $PO_2$ of blood. The cell employs pH, $PCO_2$, and $PO_2$ measuring electrodes mounted adjacent a sample passage extending through the cell. A blood sample is collected in a conventional syringe and the syringe plunger is actuated to drive the sample through the flow cell passage in contact with each of the measuring electrodes. A wash solution is then conveyed through the passage to discharge the remaining sample therefrom to prepare the flow cell for receipt of the next injected sample. In addition, a calibration solution is periodically conveyed through the passage, as required, to calibrate the measuring electrodes.

Though the foregoing apparatus represents an advance in the art of automated blood chemistry analysis, it employs a complicated array of pumps and valves for conveying the various fluids through the analyzer. When conveying blood or other biological or biochemical fluids, the valves and other elements of the control system can become contaminated or fouled by foreign material in the blood or by blood clots and are further subjected to corrosion over time by the salts and other blood components. Moreover, it is possible for dead volumes to occur in the flow system inhibiting the inefficient flow of fluid through the analyzer.

SUMMARY OF THE INVENTION

The present invention resides in a novel combined peristaltic pump and valve flow control assembly which overcomes the operational drawbacks of prior systems. The control assembly is simple in construction and operation and is subject to minimum clogging, corroding or fouling.

To these ends, the flow control assembly of the present invention is embodied in a flow control system comprising a flow cell having a passage therein for accommodating fluid flow therethrough, conduit means connected to the passage for directing fluid to and from the flow cell and peristaltic pump means including (1) an elastomeric tubular section of the conduit means and (2) a fluid driving member movable in an axial direction of and along the conduit section to pump fluid therethrough when compressed thereagainst, (3) means for selectively actuating the fluid driving member, (4) means for selectively moving one of the elastomeric tubular sections and the driving member toward and away from the other thereof to selectively define a first or pumping condition for the peristaltic pump means and a second or open flow condition through the conduit means, and (5) fluid delivery means selectively connected to the flow cell for flowing fluid through the flow cell passage and the conduit means when peristaltic pump valve means is in its second or open flow condition.

With the foregoing arrangement, the peristaltic pump means functions both as a pump and as an open valve allowing a first fluid to be conveyed through the system by the peristaltic pump and a second fluid to be conveyed by a separate pump or delivery means through the same conduit with the peristaltic pump then establishing an open channel for flow of the latter fluid. Combining the pump and valve functions in a single assembly allows effective fluid flow control without complicated valving arrangements and hence without clogging, contamination, dead volume problems being associated therewith.

DESCRIPTION OF THE PREFERRED EMBODIMENT

Figure 1:
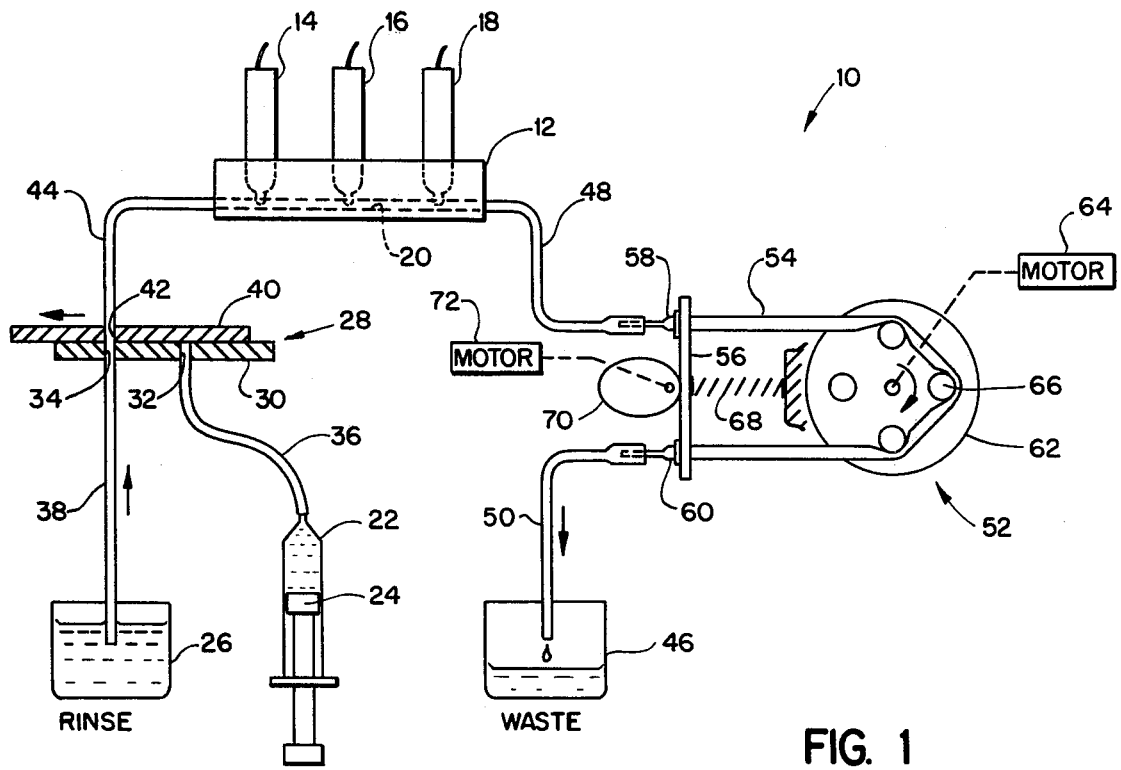
FIG. 1 is a diagram of the flow control system of the present invention and illustrates a combined peristaltic pump and valve in a first operative position as a pump.
Figure 2:
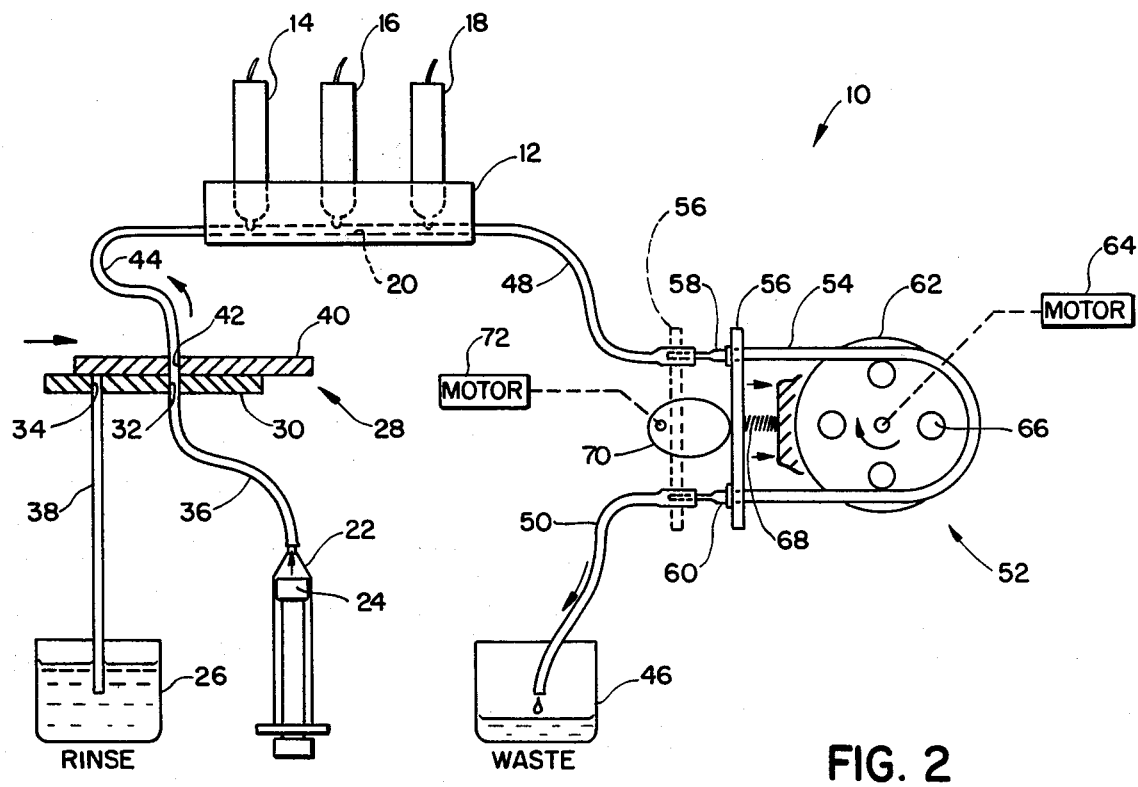
FIG. 2 illustrates the system of FIG. 1 with the combined peristaltic pump and valve in a second operative position establishing an open channel through the flow path.

As shown in the drawing for purposes of illustration, and in particular FIGS. 1-2, the present invention is embodied in a flow controller, indicated generally by numeral 10, for controlling fluid flow through a flow cell 12. The flow cell in the illustrated embodiment is of the type disclosed in the aforementioned patent for analyzing blood samples delivered to the cell but in other applications may be any other flow-type body, chamber, or other structure through which fluids are to be flowed. For blood chemistry analysis the flow cell includes a plurality of electrochemical measuring electrodes 14, 16 and 18 having their lower sensing ends positioned to contact a sample flowing through a sample passage 20 extending through the flow cell. In the disclosed flow cell, the three measuring electrodes are sensitive, respectively, to sample pH, $PCO_2$, and $PO_2$.

It will be understood that operation of such a flow cell 12 requires means for (1) delivering sample to the cell for measurement, (2) expelling sample from the cell following a measurement, and (3) flushing cell passage 20 periodically with a wash solution and/or a calibration solution or gas to prepare the measuring electrodes for the next sample measurement. To these ends, the sample is collected in a conventional syringe 22 having a plunger 24 for expelling fluid from the syringe. A wash solution reservoir 26 is provided containing the solution for flushing the sample passage 20 of the flow cell. The wash solution contains surface active agents and other agents or enzymes, as required, for conditioning and cleaning the sample passage. For further details regarding construction and operation of flow cell 12 per se, reference is made to the aforementioned patent which is specifically incorporated herein by reference.

The inlet end of the sample passage 20 is connected selectively to either sample syringe 22 or to wash solution reservoir 26 through a valve assembly 28. The valve assembly may be a conventional shear valve having a stator 30 including first and second ports 32 and 34 connected by respective conduit sections 36 and 38 to syringe 22 and reservoir 26. The valve assembly further comprises a sliding plate 40 having a single port 42 therein connected to the inlet end of sample passage 20 by conduit section 44. The sliding engagement between plate 40 and stator 30 of the valve assembly enables port 42 of the plate to be aligned either over port 32 or over port 34 of the stator to selectively connect either syringe 22 or reservoir 26 to the sample passage 20. In FIG. 1 the valve assembly is illustrated in position aligning ports 34 and 42 to supply wash solution to the flow cell.

Alternatively, valve assembly 28 may be replaced by the mechanism described in our copending application Ser. No. 922,458, for Flow Cell Fluid and Sample Supply Mechanism filed concurrently herewith, for selectively delivering sample and wash solution to the flow cell inlet.

The outlet end of sample passage 20 is connected to a waste receptacle 46 through conduit sections 48 and 50 coupled by a combined peristaltic pump and valve, indicated generally by numeral 52, in accordance with the present invention. Elements 48, 50 and 52 are arranged for the efficient delivery of fluid from the flow cell 12 toward waste receptacle 46.

Combined peristaltic pump and valve 52 includes an elastomeric tubular conduit section 54, of generally U-shape configuration, which is connected in series between conduit sections 48 and 50 to complete the flow path from the outlet of flow cell 12 to the waste receptacle 46. The opposite ends of the elastomeric tubular section are connected to a movable frame member 56. Frame member 56 is preferably of rigid construction and is mounted for movement back and forth on a support (not shown) and is guided therealong by a channel or guideway in the support. Nipple-like tubular connectors 58 and 60 attached to the frame member are inserted into the ends of respective conduit sections 48 and 50 to connect the conduit sections 48 and 50 to the elastomeric conduit section.

The peristaltic pump and valve 52 further comprises a conventional pump rotor 62 mounted on and rotated by the drive shaft of a motor 64. The rotor includes one or more rollers 66 which, in the relative position of FIG. 1, compressively engage the elastomeric tubular conduit section 54. With the elastomeric tubular section thus engaged, the bore of the conduit section is pinched at the points thereof in engagement with the rollers forming seals thereat trapping predetermined volumes of fluid in the portions of tubular conduit 54 between the pump rollers. Clockwise rotation of the pump rotor in response to actuation of motor 64 then functions to pump the trapped volumes of fluid through the conduit 54 in a conventional manner.

In accordance with an important aspect of the invention, the relative position of the elastomeric tubular section 54 and the pump rotor 62 may be adjusted to a position wherein the rollers 66 are effectively released from the conduit 54 to open the seals therein establishing an open channel through the elastomeric tubular section 54 for fluid otherwise pumped or driven through the system. To this end, frame member 56 is engaged on one side by a compressed spring 68 and on the opposite side by an eccentric cam 70 mounted on and rotated by the drive shaft of a motor 72. Spring 68 biases the movable frame member to the left in FIG. 1 and cooperates with the illustrated low point of cam 70 to define the position of frame member 54 at which elastomeric tubular section 54 is pulled sufficiently taut around pump rollers 66 to enable peristaltic pump action upon rotation of the pump rotor 62. In order to release the compressive engagement between the elastomeric tubular section 54 and the pump rotor, cam 70 is rotated 180° to the position illustrated in FIG. 2 to drive the frame member 56 and hence drive conduit section 54 secured thereto a sufficient distance to the right in FIG. 2 against the bias of compression spring 68 to relax the compressive engagement between conduit section and rotor. Thus relaxed, elastomeric tubular section 54 defines an open flow channel for accommodating fluid flow between flow cell 12 and waste receptacle 46. Specifically, in the preferred embodiment, the open flow channel is adapted to accommodate fluid flow toward waste receptacle 46 as driven through the system by the action of plunger 24 of syringe 22. To this end, with an open channel in elastomeric conduit section 54, valve assembly 28 is switched to the position of FIG. 2 connecting sample syringe 22 to the inlet of flow cell 12. Syringe plunger 24 is depressed, either manually or automatically, to drive blood sample into the flow cell through sample passage 20. Such sample flow is possible because the open channel provided in elastomeric tubular section 54 enables fluid in the system downstream of the injected sample to be driven through the open channel toward the waste receptacle by the act of depressing the syringe plunger.

The flow control arrangement operates in the following manner. Assume first that flow cell 12 has not been prepared for sample injection. Accordingly, valve assembly 28 is switched to the position of FIG. 1 connecting wash solution reservoir 26 to the inlet end of sample passage 20. Cam 70 is rotated to the position of FIG. 1 allowing compression spring 68 to drive frame member 54 to the position pulling elastomeric tubular section 54 into compressive engagement with pump rollers 66. The pump rotor is then driven clockwise to draw wash solution from reservoir 26 through conduit sections 38 and 44, into and through sample passage 20 of the flow cell and into conduit section 48 (and 54 and 50 if necessary) toward waste receptacle 46. With the sample passage thus flushed and prepared for a measurement, valve assembly 28 is switched to the position of FIG. 2 connecting the flow cell inlet to syringe 22. Cam 70 is rotated 180° to the position of FIG. 2 driving frame member 54 and the elastomeric tubular section to the right against the bias of spring 68 to relax elastomeric tubular section 54 and provide an open channel therethrough. Thereafter, syringe plunger 24 is depressed forcing the blood sample through conduit sections 36 and 44 into and through sample passage 20 past the measuring electrodes 14–18. Material in the conduits ahead of the injected sample is pushed therethrough toward waste receptacle 46 by the blood sample in response to depression of syringe plunger 24. Such passage of fluid toward the waste receptacle is accommodated by the open channel defined in the elastomeric tubular section 54 of the combined peristaltic pump and valve assembly 52.

It is thus seen that by combining the peristaltic pump and valve into a common assembly for both pumping fluid through the system and for accommodating flow of fluid otherwise conveyed through the system, there is no need for other valving between the flow cell 12 and the waste receptacle 46 and the fluid delivery through the system is rapid and efficient and free of dead volumes associated with prior valves. Moreover, the combined peristaltic pump and valve is not subject to the corrosion and clogging problems associated with other valving thus increasing the operational life and easing the maintenance problems associated with chemical analyzers or other systems adopting the present flow control arrangement.

Figure 3:
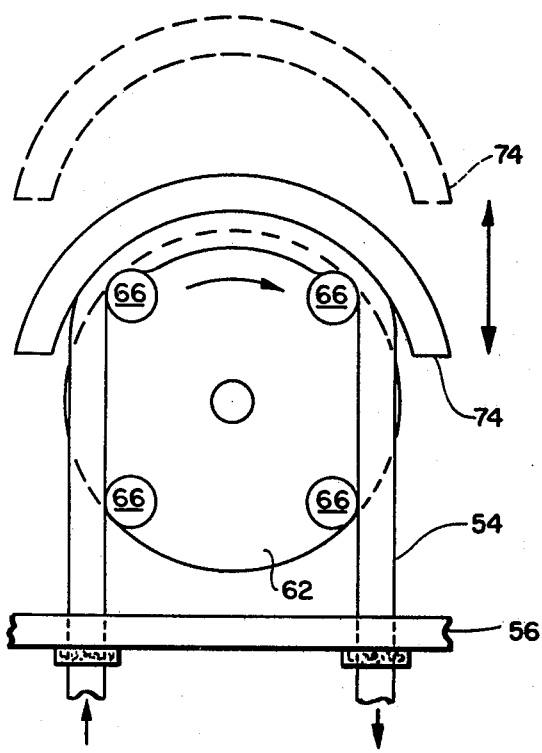
FIGS. 3 and 4 illustrate alternative forms of a combined peristaltic pump and valve assembly for use in the system of FIGS. 1 and 2.
Figure 4:
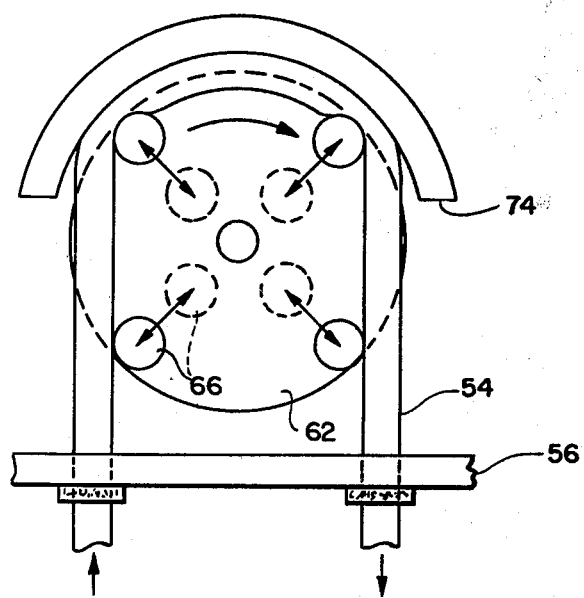

FIGS. 3 and 4 illustrate two alternative arrangements for a combined peristaltic pump and valve 52 for incorporation in the system of FIGS. 1-2. In these figures, like numerals have been used to identify elements common to FIGS. 1-2. In both FIGS. 3-4, the elastomeric tubular section 54 is compressed between peristaltic pump rotor rollers 66 and an arcuate pressure plate or back-up shoe 74. The inner circumferential surface of the pressure plate is coaxial with the axis of rotation of the pump rotor. With elastomeric tubular section 54 compressively engaged between the pump rotor rollers and the pressure plate in each of FIGS. 3-4, rotation of the rotor pumps the thus trapped volumes of fluid through the conduit section. The illustrated positions of FIGS. 3-4 thus correspond to the pumping condition for the peristaltic pump.

In both FIGS. 3-4, the frame member 56 supporting elastomeric tubular section 54 is rigidly fixed to a support (not shown). In order to release the compressive engagement on the tubular section 54, in FIG. 3, pressure plate 74 is moved to the position illustrated in phantom outline thereby allowing elastomeric tubular section 54 to move slightly upward in the figure out of compressive engagement with pump rollers 66. In FIG. 4 the pressure plate 74 is stationary, and the pump rollers 66 are adjustable to positions radially inward of their pumping positions as illustrated in phantom outline in the figure. This likewise provides relative motion between the rollers and the tubular section releasing the compressive engagement therebetween and establishing the open flow channel through the section. The mechanical apparatus for effecting the foregoing pressure release in FIGS. 3-4 is straightforward in principle and construction.

It will be understood that operation of flow cell 12, as described in the aforementioned patent, further includes periodic pumping of a calibration solution through the sample passage 20 to calibrate the measuring electrodes 14-18, as necessary. The calibration solution comprises a predetermined and physiological normal concentration of the particular blood components or ions being measured. It will be understood that valve assembly 28 may include an additional port in stator 30 for selectively connecting a calibration solution reservoir, when required, to the inlet of sample passage 20, and that pump rotor 62 would be actuated to draw the calibration solution through the flow cell. Moreover, while a preferred embodiment of the invention has been illustrated and described, various modifications may be made therein without departing from the spirit and scope of the invention as defined by the appended claims.

What is claimed is:
1. A fluid flow control system comprising:
   a flow cell having a passage therein for accommodating fluid flow therethrough;
   conduit means connected to said passage for directing fluid to and from said flow cell, said conduit means including an elastomeric tubular section;
   peristaltic pump-valve means including (1) said elastomeric tubular section of said conduit means, (2) a fluid driving member movable along said section to pump fluid therethrough when compressed thereagainst, (3) means for actuating said fluid driving member, and (4) means for selectively moving one of said section and driving member toward and away from the other thereof to selectively define a first or pumping condition for said peristaltic pump with said driving member compressed against said section and a second or open flow condition through said conduit means;
   fluid delivery means selectively connected to said flow cell for flowing fluid through said flow cell passage and said conduit means when said peristaltic pump-valve means is in its second condition;
   a fluid reservoir, and
   means for selectively connecting said fluid delivery means or said fluid reservoir to said flow cell, said peristaltic pump-valve means in said first condition being actuable to pump a first fluid from said reservoir through said flow cell passage and in said second condition accommodating flow of a second fluid through said flow cell passage in response to said fluid delivery means.

2. The fluid flow control system of claim 1 wherein said fluid delivery means comprises a syringe and movable syringe plunger for driving fluid from the syringe and through the flow cell.

3. The fluid flow control system of claim 1 further including:
   a fluid receptacle in fluid connection with said conduit means for receiving therefrom (1) said first fluid pumped through said flow cell by said peristaltic pump-valve means in said first condition, and (2) said second fluid flowed through said flow cell by said fluid delivery means as accommodated by said peristaltic pump-valve means in said second condition.

4. The fluid flow control system of claim 1 wherein said fluid driving member comprises a rotor having compressive surfaces engaging said tubular section at spaced points thereon, and means for rotating said rotor for moving said compressive surfaces therealong to pump fluid therethrough.

5. The fluid flow control system of claim 4 further including a pressure plate for engaging said elastomeric tubular section on a side thereof opposite the engagement thereof by said compressive surfaces of said rotor.

6. The flow control system of claim 5 including means for moving said pressure plate in a direction away from said elastomeric tubular section allowing relative movement between said tubular section and said pump rotor.

7. The fluid flow control system of claim 5 wherein said pump rotor includes a plurality of rollers mounted thereon defining said compressive surfaces, and means for moving said rollers radially inward in a direction away from said tubular section.

8. A peristaltic pump-valve assembly including: (1) conduit means having an elastomeric tubular section, (2) a fluid driving member movable along said section to pump fluid therethrough when compressed thereagainst, (3) means for actuating said fluid driving member, (4) means for selectively moving one of said section and driving member toward and away from the other thereof to selectively define a first or pumping condition for said peristaltic pump and valve with said driving member compressed against said section and a second or open flow condition through said conduit means, and fluid delivery means connected to said conduit means for flowing fluid through said elastomeric tubular section thereof when said peristaltic pump valve is in its second condition;
a fluid reservoir; and
means for selectively connecting said fluid delivery means or said fluid reservoir to said conduit means, said peristaltic pump-valve means in said first condition being actuable to pump a first fluid from said reservoir through said conduit means and in said second condition accommodating flow of a second fluid through said conduit means in response to said fluid delivery means.

* * * * *